(12) United States Patent  
Farascioni et al.

(10) Patent No.: US 9,186,137 B2  
(45) Date of Patent: Nov. 17, 2015

(54) CARTRIDGE SHIPPING AID

(71) Applicant: Covidien LP, Mansfield, MA (US)

(72) Inventors: David Farascioni, Bethel, CT (US);
Dino Kasvikis, Mansfield, MA (US);
Russell Estrella, Hamden, CT (US);
Michael Robbins, New Haven, CT (US); Jonathan Sapienza, Orange, CT (US)

(73) Assignee: Covidien LP, Mansfield, MA (US)

( * ) Notice: Subject to any disclaimer, the term of this patent is extended or adjusted under 35 U.S.C. 154(b) by 94 days.

(21) Appl. No.: 14/246,496

(22) Filed: Apr. 7, 2014

(65) Prior Publication Data

US 2014/0216964 A1 Aug. 7, 2014

Related U.S. Application Data

(63) Continuation of application No. 12/964,898, filed on Dec. 10, 2010, now Pat. No. 8,714,352.

(51) Int. Cl.
*B65D 85/24* (2006.01)
*A61B 17/068* (2006.01)
(Continued)

(52) U.S. Cl.
CPC .............. *A61B 17/068* (2013.01); *A61B 17/072* (2013.01); *A61B 19/026* (2013.01); *A61B 2017/0688* (2013.01); *A61B 2017/07221* (2013.01); *A61B 2017/07235* (2013.01); *A61B2017/07271* (2013.01); *A61B 2019/0202* (2013.01); *A61B 2019/0212* (2013.01)

(58) Field of Classification Search
CPC ... B43M 9/009; A61B 17/068; A61B 19/026; A61B 17/105; A61B 2017/0688; A61B 2017/07271

USPC ......... 206/338–341, 345–348, 230, 363, 438, 206/561, 509, 384, 385, 63.5, 557, 563; 220/780, 315, 23.2, 23.4, 7, 574, 575; 227/901, 175.1, 178.1, 111, 127, 140, 227/179.1, 181.1, 176.1, 145; 606/75, 322
See application file for complete search history.

(56) References Cited

U.S. PATENT DOCUMENTS 4,512,468 A    4/1985   Stravitz
D349,977  S    8/1994   Shen
(Continued)

FOREIGN PATENT DOCUMENTS

EP    2018826 A2    1/2009
EP    2172157 A1    4/2010
WO    99/49804 A1   10/1999

OTHER PUBLICATIONS

European Search Report EP11192800 dated Mar. 22, 2013.

*Primary Examiner* — Jacob K Ackun
*Assistant Examiner* — Rafael Ortiz

(57) ABSTRACT

A cartridge shipping aid is provided to retain staples within staple pockets of a staple cartridge during shipment. The cartridge shipping aid includes a base and a longitudinal rib extending perpendicularly from an underside of the base and indiscernible into a knife slot formed in a staple cartridge. One or more perpendicular keys are formed along a lower edge of the longitudinally extending rib for engagement with an underside surface of the staple cartridge. The cartridge shipping aid may additionally include sidewalls projecting perpendicularly from outer edges of the base. Projections are formed on one end of the base for engagement with associate detents formed on the staple cartridge. Grasping structure is formed adjacent one end of the base and longitudinal rib.

18 Claims, 12 Drawing Sheets

(51) Int. Cl.
*A61B 17/072* (2006.01)
*A61B 19/02* (2006.01)

(56) References Cited

U.S. PATENT DOCUMENTS

| | | |
|---|---|---|
| 5,443,160 A | 8/1995 | Tortorella et al. |
| 5,474,180 A | 12/1995 | Robinson et al. |
| 6,585,144 B2 | 7/2003 | Adams et al. |
| 6,662,949 B2 | 12/2003 | Zheng et al. |
| 7,147,140 B2 | 12/2006 | Wukusick et al. |
| 2002/0020732 A1 | 2/2002 | Adams et al. |
| 2004/0094597 A1 | 5/2004 | Whitman et al. |
| 2007/0114261 A1 | 5/2007 | Ortiz et al. |
| 2008/0302854 A1 | 12/2008 | Rethy et al. |
| 2009/0114701 A1 | 5/2009 | Zemlok et al. |
| 2009/0277947 A1 | 11/2009 | Viola |
| 2010/0127040 A1 | 5/2010 | Smith et al. |

CARTRIDGE SHIPPING AID

CROSS-REFERENCE TO RELATED APPLICATIONS

This application is a continuation and claims the benefit of and priority to U.S. patent application Ser. No. 12/964,898, filed Dec. 10, 2010 the entire disclosure of which is incorporated by reference herein.

BACKGROUND

1. Technical Field

The present disclosure relates to staple cartridge covers or shipping aids. More particularly, the present disclosure relates to removable cartridge shipping aids for keeping staples and staple pushers properly positioned within a staple cartridge prior to assembly.

2. Background of Related Art

Certain surgical procedures often require forming lines of staples through tissue sections and, in some instances, severing the tissue between the staple lines with a knife blade. Some surgical staplers typically include a removable staple containing cartridge for use with a surgical instrument. The removable staple cartridge generally includes an outer support or frame member and an insert containing one or more rows of staple containing pockets. In some cases, a staple cartridge includes a plurality of longitudinally staggered rows of staple containing pockets. When severing tissue between the rows of stapled tissue, a knife slot extends between the plurality of rows of staple containing pockets.

The staple containing pockets formed in the insert are open to the tissue engaging surface of the insert and contain staples and pushers for ejecting the staples out of the staple cartridge. The staples are generally maintained within the staple containing pockets such that tissue penetrating tips of the staples lie beneath or flush with the tissue engaging surface of the insert.

As noted above, some surgical instruments are configured to utilize removable staple cartridges. These removable staple cartridges are usually packaged and shipped separately and independently of the surgical stapler. Occasionally, these staples and pushers contained within the staple cartridge may be jostled or shaken loose such that the tissue penetrating tips of the staples project upwardly from the tissue engaging surface, or they fall out of the staple cartridge entirely. Where the staples project upwardly from the tissue engaging surface, it may not be noticed prior to use of the staple cartridge, but may cause the tissue penetrating tips of the staples to catch or snag on tissue as the staple cartridge is positioned about the tissue.

Some surgical staplers utilize loading units that include a staple-containing cartridge and an anvil assembly. The staple cartridge may be loaded with staples and handled during manufacturing.

Thus, there exists a need for a shipping aid or cover to prevent staples and associated pushers from shifting out of staple containing pockets during handling or shipment and prior to assembly of the staple cartridge with a surgical staple.

SUMMARY

There is disclosed a cartridge shipping aid for use in retaining staples and pushers within a staple cartridge. The cartridge shipping aid generally includes a base, a first sidewall extending perpendicularly from a first edge of the base and a second sidewall extending perpendicularly from a second edge of the base. A rib extends perpendicularly from an underside of the base and extends parallel to the first and second side walls. The rib includes at least one perpendicular key formed along a bottom edge of the rib for engagement with the underside of the staple cartridge.

The base further includes a tab extending from a first end of the base and a T-shaped tab extending from a second end of the base. The T-shaped tab also includes a downward projection for engagement with a staple cartridge. Specifically, the downward projection includes at least one pin for engagement with a detent formed in a staple cartridge. The T-shaped tab also includes a cross member and a flexible neck connecting the cross member to the second end of the base and the downward projection extends from the cross member.

In a specific embodiment, the base, first and second sidewalls and rib are curved. The radius of curvature of the base, first and second side walls and rib are substantially the same as identical to the radius of curvature of an associated staple cartridge.

There is also disclosed a cartridge shipping aid having a base, a first sidewall extending perpendicularly from the base and having a first inwardly directed lip and a second sidewall extending perpendicularly from the base and having a second inwardly directed lip.

In a particular embodiment, the base includes at least one rib extending perpendicularly from an underside of the base and extending parallel to the first and second side walls. In a more specific embodiment, a plurality of longitudinally spaced ribs extends perpendicularly from the underside of the base.

In one particular embodiment, the at least one rib includes a perpendicular key formed on a lower edge of the at least one rib for engagement with the underside of the staple cartridge.

In a still more specific embodiment, the first sidewall of the cartridge shipping aid includes at least one downward projection and the inwardly directed lip extends from the at least one downward projection.

There is still further disclosed a cartridge shipping aid having a longitudinally extending base and a longitudinal rib extending perpendicularly from an underside of the base. A grasping structure extends from proximal ends of the longitudinally extending base and longitudinal rib. The longitudinal rib includes a leading tooth extending from a distal end of the longitudinal rib to facilitate insertion of the longitudinal rib into a knife slot formed in a staple cartridge.

The grasping structure includes a cut-out. The grasping structure additionally includes a rib extension and a perpendicular flange formed on the rib extension for engagement with the underside of the staple cartridge.

DESCRIPTION OF THE DRAWINGS

Various embodiments of the presently disclosed cartridge shipping aid are disclosed herein with reference to the drawings, wherein.

DETAILED DESCRIPTION OF EMBODIMENTS

Embodiments of the presently disclosed cartridge shipping aids will now be described in detail with reference to the drawings wherein like numerals designate identical or corresponding elements in each of the several views. As is common in the art, the term "proximal" refers to that part or component closer to the user or operator, i.e., surgeon or physician while the term "distal" refers to that part or component further away from the user.

Figure 1:
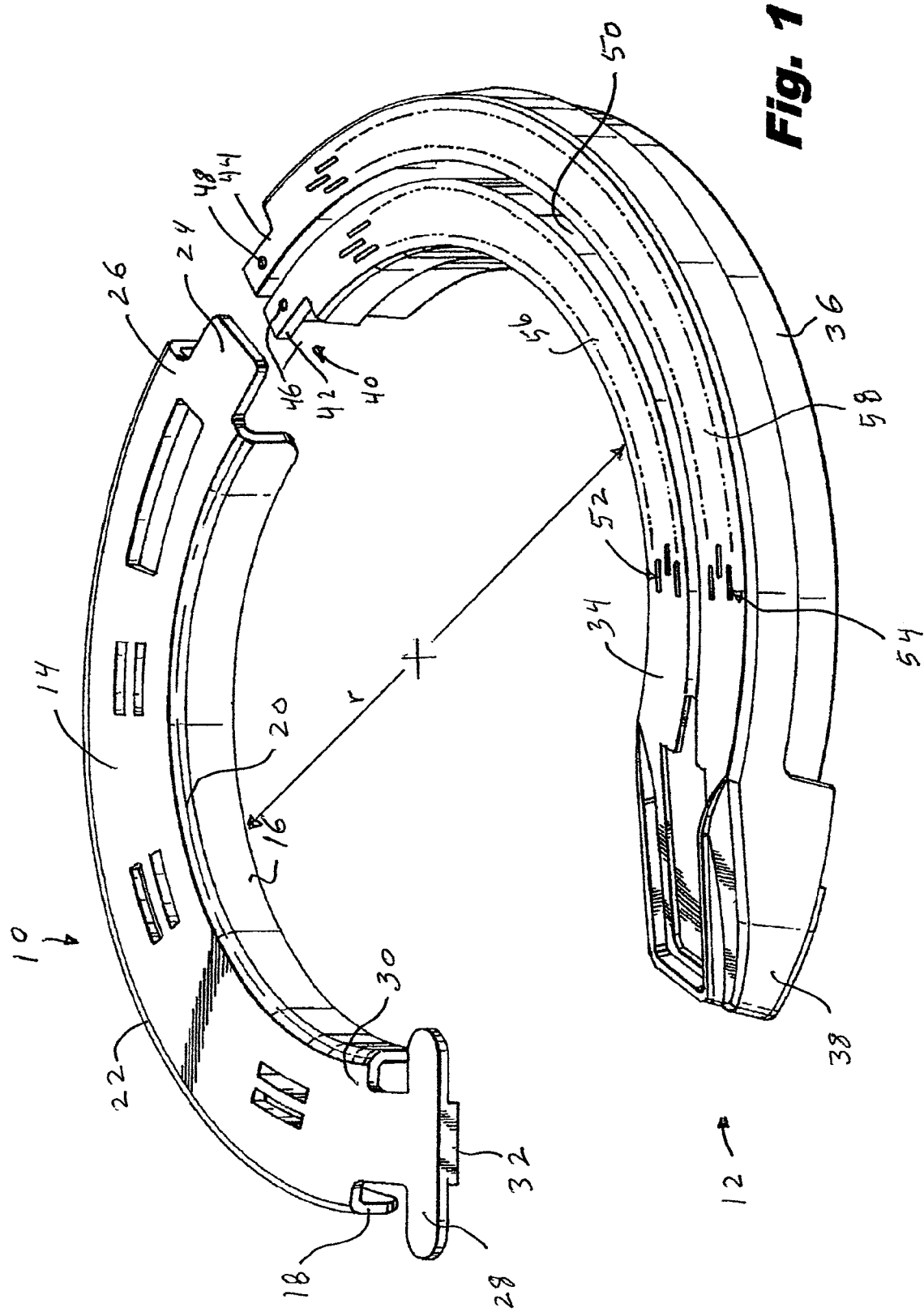
FIG. 1 is a perspective view of one embodiment of a cartridge shipping aid and a staple cartridge.

Referring initially to FIG. 1, there is disclosed a cartridge shipping aid 10 for use with a staple cartridge 12. Cartridge shipping aid 10 is provided to maintain various components of staple cartridge 12 in place prior to assembly. Cartridge shipping aid 10 generally includes a base 14 having first and second sidewalls 16 and 18 extending perpendicularly from respective first or inner and second or outer edges 20 and 22 of base 14. A straight tab 24 extends from a first end 26 of base 14 and T-shaped tab 28 extends from a second end of base 14. T-Shaped tab 28 includes a downward projection 32 for engagement with staple cartridge 12.

Staple cartridge 12 generally includes an insert 34 positioned within an outer channel member or plate 36. Insert 34 is preferably formed of a plastic material while outer channel member or plate 36 is formed from a metallic material. Insert 34 includes an angle leading edge 38 and a trailing projection 40. Trailing projection 40 includes first and second projection halves 42 and 44. First and second projection halves 42 and 44 include respective first and second detents 46 and 48 engagement with corresponding structure on cartridge shipping aid 10. Insert 34 additionally includes a knife slot 50 which extends between first and second projection halves 42 and 44 and substantially the length of insert 34 to angled leading edge 38. Pluralities of staple containing pockets 52 and 54 are provided in respective inner and outer upper surfaces 56 and 58 of insert 34.

The shipping aid 10 shown in FIG. 1 has a curved shape, and the staple cartridge 12 has a curved shape. In other embodiments, the shipping aid 10 is shaped to cooperate with a linear staple cartridge, and has a rectangular shape. Other shapes are contemplated.

As shown, cartridge shipping aid 10 and staple cartridge 12 are formed with arcuate shapes. In order to position cartridge shipping aid 10 about staple cartridge 12, cartridge shipping aid 10 and staple cartridge 12 have a common radius "r".

Figure 2:
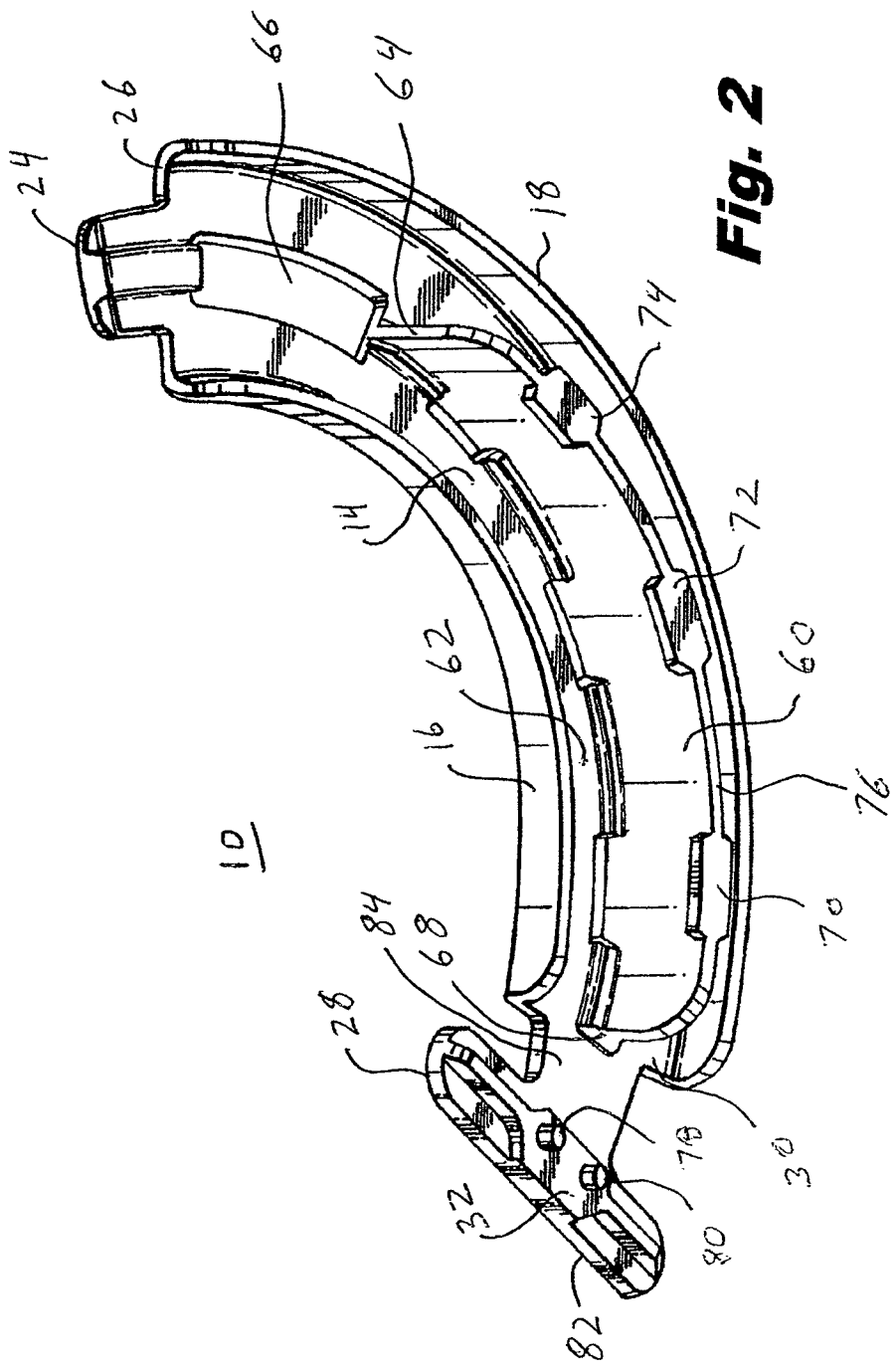
FIG. 2 is a perspective view, taken from below, of the cartridge shipping aid of FIG. 1.
Figure 3:
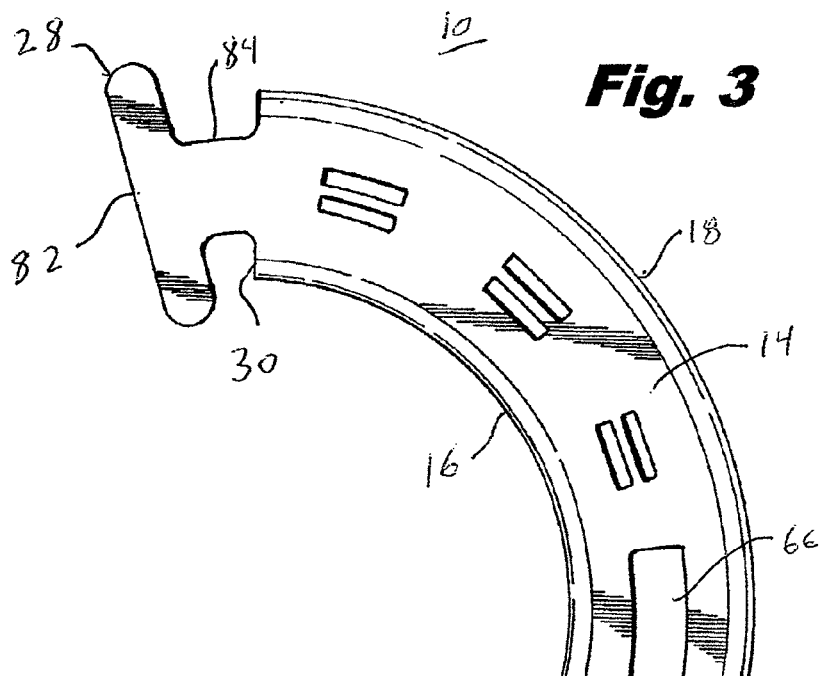
FIG. 3 is a top plan view of the cartridge shipping aid of FIG. 1.
Figure 4:
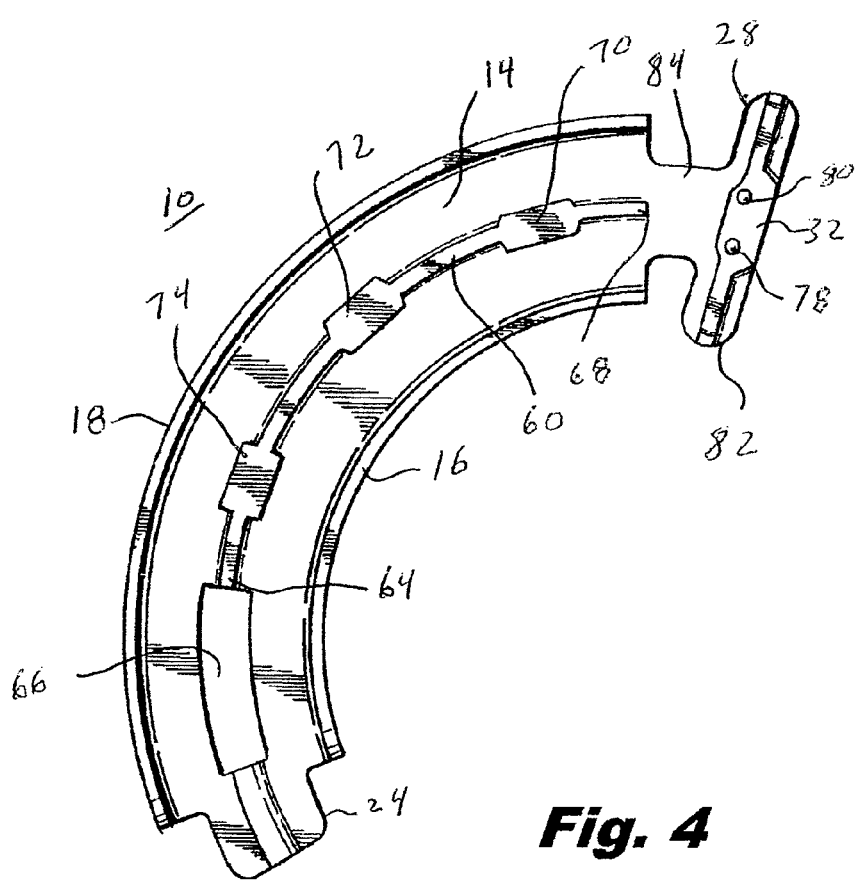
FIG. 4 is a bottom plan view of the cartridge shipping aid of FIG. 1.

Referring now to FIGS. 2, 3 and 4, and initially with regard to FIGS. 2 and 4, in order to guide and secure cartridge shipping aid 10 onto staple cartridge 12, a central wall or rib 60 extends perpendicularly from an undersurface 62 of base 14. Rib 60 runs essentially parallel to first and second sidewalls 16 and 18. A first end 64 of rib 60 is proximal of first end 26 of base 14 and is adjacent an opening 66. Rib 60 extends from first end 64 to a second end 68 adjacent second end 30 of base 14. Rib 60 rides within knife slot 50 in staple cartridge 12 to guide cartridge shipping aid 10 along staple cartridge 12. In order to prevent cartridge shipping aid 10 from lifting off of staple cartridge 12 vertically, rib 60 includes perpendicular flanges or keys 70, 72 and 74 which are formed perpendicular to, and on a bottom surface 76 of, rib 60. Keys 70, 72 and 74 engage an undersurface of plastic insert 34 of staple cartridge 12 in a manner described in more detail below.

In order to secure cartridge shipping aid 10 against longitudinal movement along staple cartridge 12, a pair of pins 78 and 80 project from downward projection 32 of T-shaped tab 28 and are configured to engage detents 46 and 48 formed in projection halves 42 and 44 of trailing projection 40 on staple cartridge 12.

Referring to FIGS. 2, 3 and 4, it should be noted that T-shaped tab 28 includes a cross member 82 and a flexible neck 84 connecting crossmember 82 to second end 30 of base 14. Flexible neck 84 allows an operator to grasp and lift crossmember 82 in order to pull pins 78 and 80 out of detents 46 and 48 in order to release cartridge shipping aid 10 for longitudinal movement relative to staple cartridge 12. Additionally, as shown, due to the curvature of cartridge shipping aid 10, the length of second side wall 18 is longer than the length of first side wall 16.

Referring now to FIGS. 1, 2 and 5-7, and initially with regard to FIGS. 1 and 2, the operation of cartridge shipping aid 10 to shield first and second pluralities of staple pockets 52 and 52, in staple cartridge 12, will now be described. With reference to FIG. 1, cartridge shipping aid 10 is positioned adjacent staple cartridge 12 such that first end 26 of base 14 is adjacent trailing projection 40 of staple cartridge 12. Cartridge shipping aid 10 is then rotated or moved longitudinally such that rib 60 (FIG. 2) enters knife slot 50.

Figure 5:
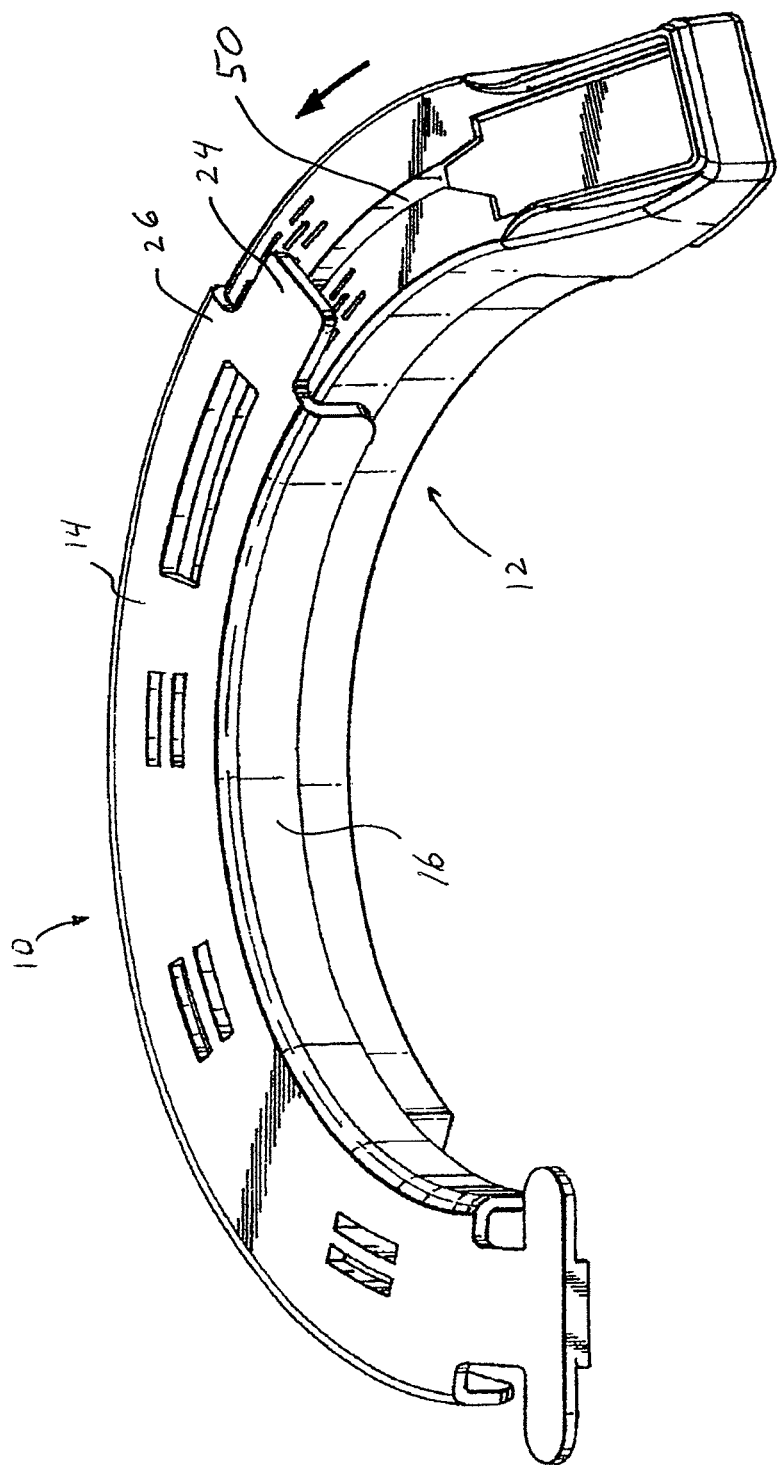
FIG. 5 is a perspective view of the cartridge shipping aid of FIG. 1 being positioned onto the staple cartridge.
Figure 6:
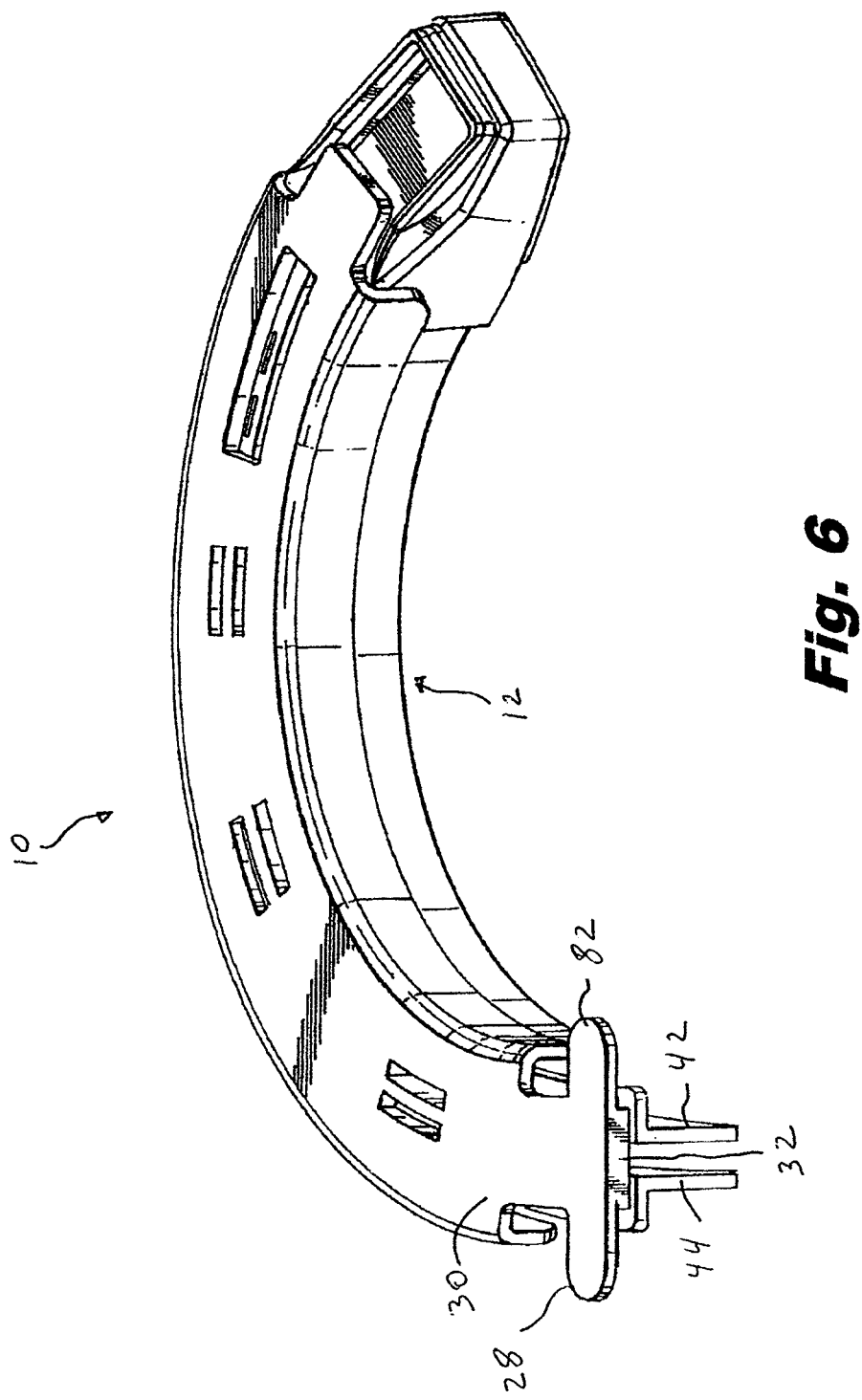
FIG. 6 is a perspective view of the cartridge shipping aid of FIG. 1 fully seated on the staple cartridge.
Figure 7:
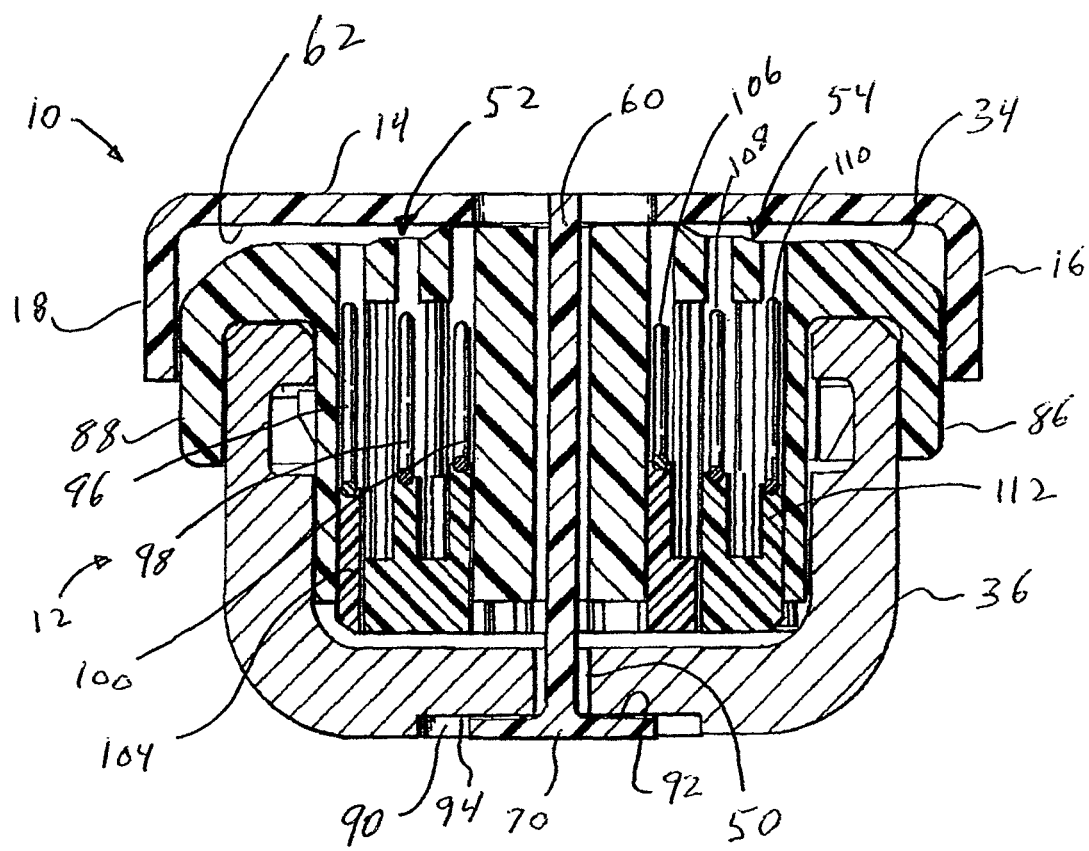
FIG. 7 is a cross sectional view of the cartridge shipping aid of FIG. 1 seated on the staple cartridge.

Referring now to FIGS. 5 and 6, thereafter, cartridge shipping aid 10 continues to be slid longitudinally relative to staple cartridge 12. First and second side walls 16 and 18 of cartridge shipping aid 10 ride along outer sidewalls 86 and 88 of plastic insert 34 (FIG. 7). Cartridge shipping aid 10 is advanced until T-shaped tab 28 is flush with trailing projection halves 42 and 44 (FIG. 6). As noted herein above, cartridge shipping aid 10 includes pins 78 and 80 on T-shaped tab 28 which are received and secured within detents 46 and 48 formed in projection halves 42 and 44 to thereby secure cartridge shipping aid 10 against further longitudinal motion relative to staple cartridge 12.

Referring now to FIG. 7, as rib 60 slides within knife slot 50, perpendicular keys 70, 72 and 74, formed on bottom surface 76 of rib 60, slide within a horizontal slot 90 formed in outer channel member 36 such that an upper surface 92 of perpendicular key 70 is restrained from vertical movement by a bottom surface 94 of outer channel member 36.

As shown, a plurality of staples 96, 98 and 100 are positioned within plurality of staple pockets 52 and are supported by pushers 104. Similarly, a plurality of staples 106, 108 and 110 are supported within plurality of staple pockets 54 and be supported therein by pushers 112. In this particular embodiment, the individual staples such as, for example, staples 96, 98 and 100 are of varying sizes. Once cartridge shipping aid 10 has been fully positioned about staple cartridge 12 it can be seen that undersurface 62 of base 14 of cartridge shipping aid 10 is positioned above plurality of staple pockets 52 and 54 to thereby secure the staples and associated pushers within staple cartridge 12.

When the combined staple cartridge 12 and cartridge shipping aid 10 are to be used, first member 82 of T-shaped tab 28 is lifted to draw ends 78 and 80 (FIG. 2) out of engagement of detents 46 and 48 formed in projection halves 42 and 44 thereby freeing cartridge shipping aid 10 for longitudinal movement relative to, and removal from, staple cartridge 12.

In this manner, cartridge shipping aid 10 firmly and positively secures staples contained within staple cartridge 12 to prevent movement relative to staple cartridge 12 prior to assembly with a surgical instrument.

Figure 8:
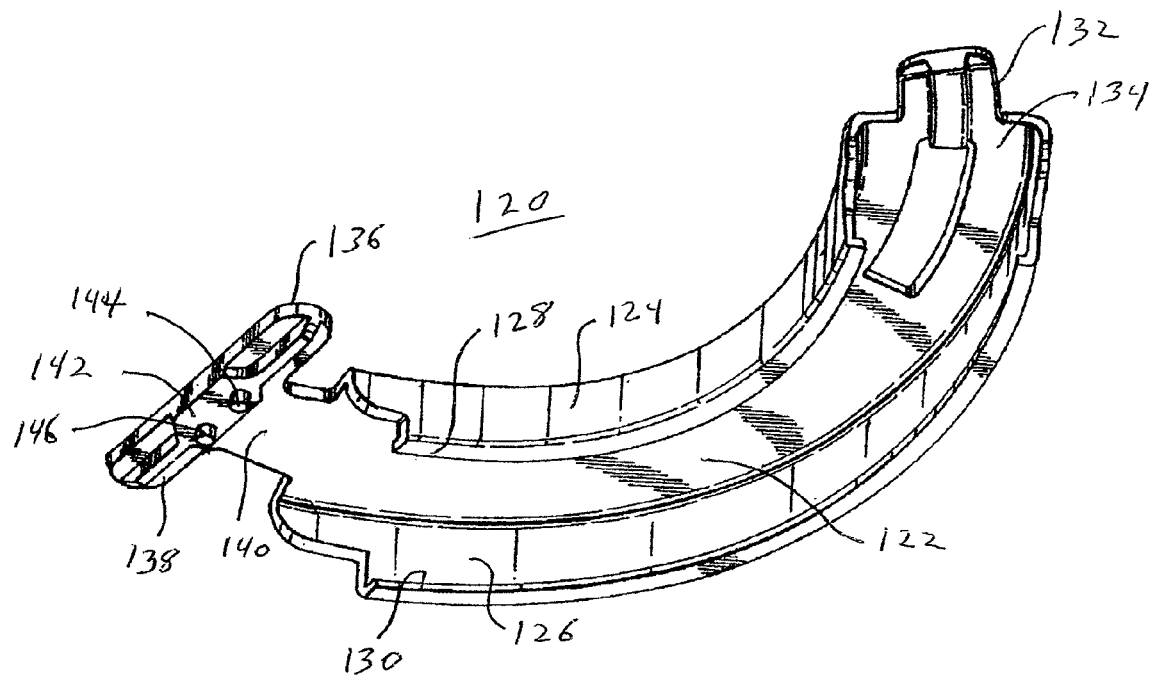
FIG. 8 is a perspective view, taken from below, of another embodiment of a cartridge shipping aid.
Figure 9:
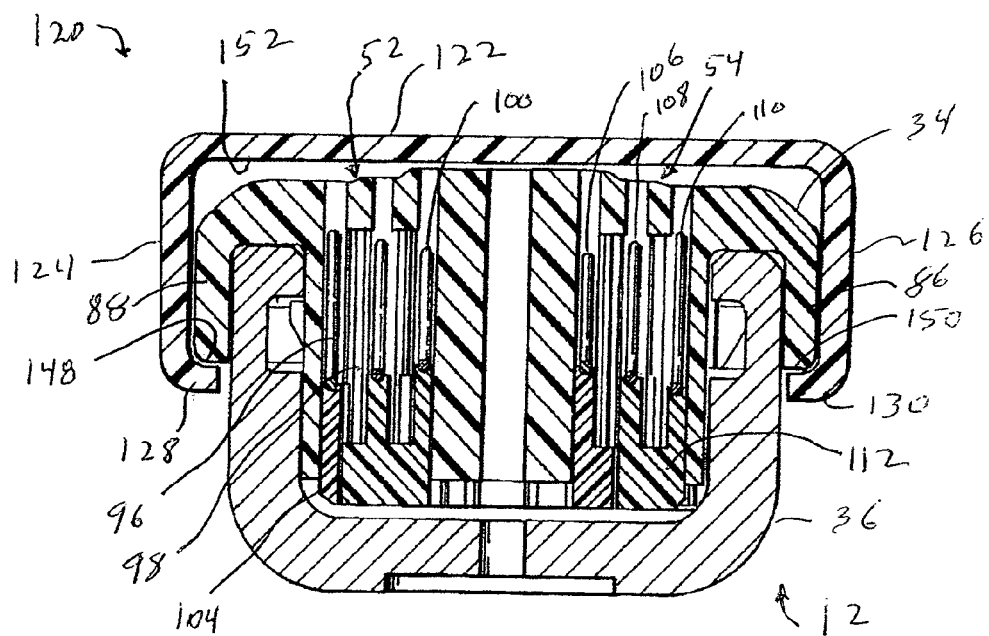
FIG. 9 is a cross sectional view of the cartridge shipping aid of FIG. 8 positioned on a staple cartridge.

Referring now to FIGS. 8 and 9, there is disclosed an alternative embodiment of a cartridge shipping aid 120. Although the shipping aid 120 shown has a curved shape, and the staple cartridge 12 has a curved shape, rectangular and other shapes are contemplated. Cartridge shipping aid 120 includes a base 122 and first and second side walls 124 and 126 extending perpendicularly from base 122. In this embodiment, first and second sidewalls 124 and 126 include respective inwardly directed lips 128 and 130 to engage structure on staple cartridge 12 in a manner described hereinbelow. Similar to cartridge shipping aid 10 described herein above, cartridge shipping aid 120 includes a tab 132 formed on a first end 134 of base 122. Cartridge shipping aid 120 additionally includes a T-shaped tab 136 having a cross member 138 and a flexible neck 140. A downward projection 142 extends from cross member 138 and includes pins 144 and 146 for engagement with the detents 46 and 48 formed within trailing projections 40 and 42 and staple cartridge 12.

In this embodiment, cartridge shipping aid 20 may be assembled onto staple cartridge 12 by aligning first end 132 of base 122 with trailing projections 40 and 42 on insert 34. Cartridge shipping aid 120 may then be rotated relative to staple cartridge 12 in a manner described herein above with regard to cartridge shipping aid 10. As cartridge shipping aid 120 is rotated, inwardly directed lips 128 and 130 formed in first and second side walls 124 and 126, respectively, engage and is secured by bottom edges 148 and 150 of sidewalls 86 and 88 of insert 34.

Alternatively, first and second side walls 124 and 126 may be sufficiently flexible relative to base 122 such that cartridge shipping aid 120 may be brought vertically down onto staple cartridge 12 to cause first and second sidewalls 124 and 126 to flex outwardly relative to sidewalls 86 and 88 of insert 34. Once fully seated, inwardly directed lips 128 and 130 of first and second sidewalls 124 and 126 snap around side walls 86 and 88 of insert 34 such that inwardly directed lips 128 and 130 engage bottom edges 148 and 150 of sidewalls 86 and 88.

Thus, cartridge shipping aid 20 may be positioned about staple cartridge 12 in either or both different manners. As shown, an undersurface 152 of cartridge shipping aid 120 covers and secures plurality of staples 96, 98, 100, 106, 108 and 110 within plurality a staple pockets 52 and 54 along with staple pushers 104 and 112.

Figure 10:
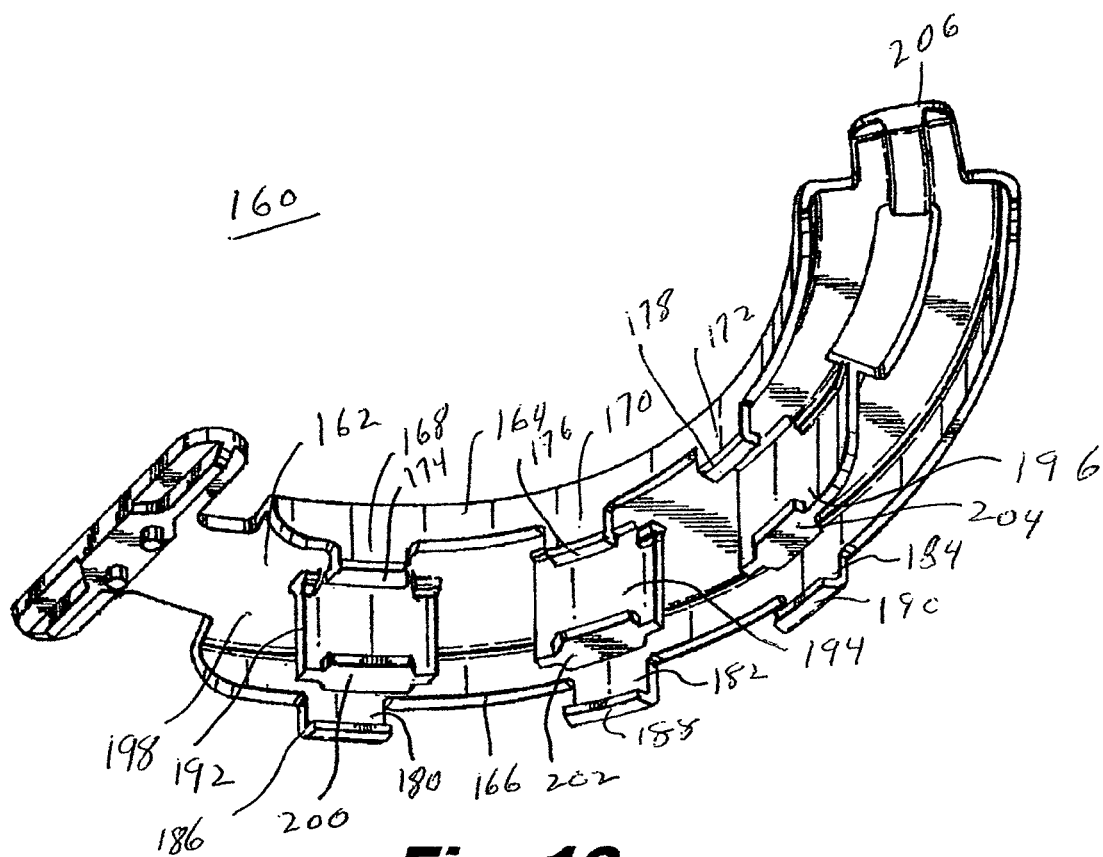
FIG. 10 is a perspective view, taken from below, of a further embodiment of a cartridge shipping aid.
Figure 11:
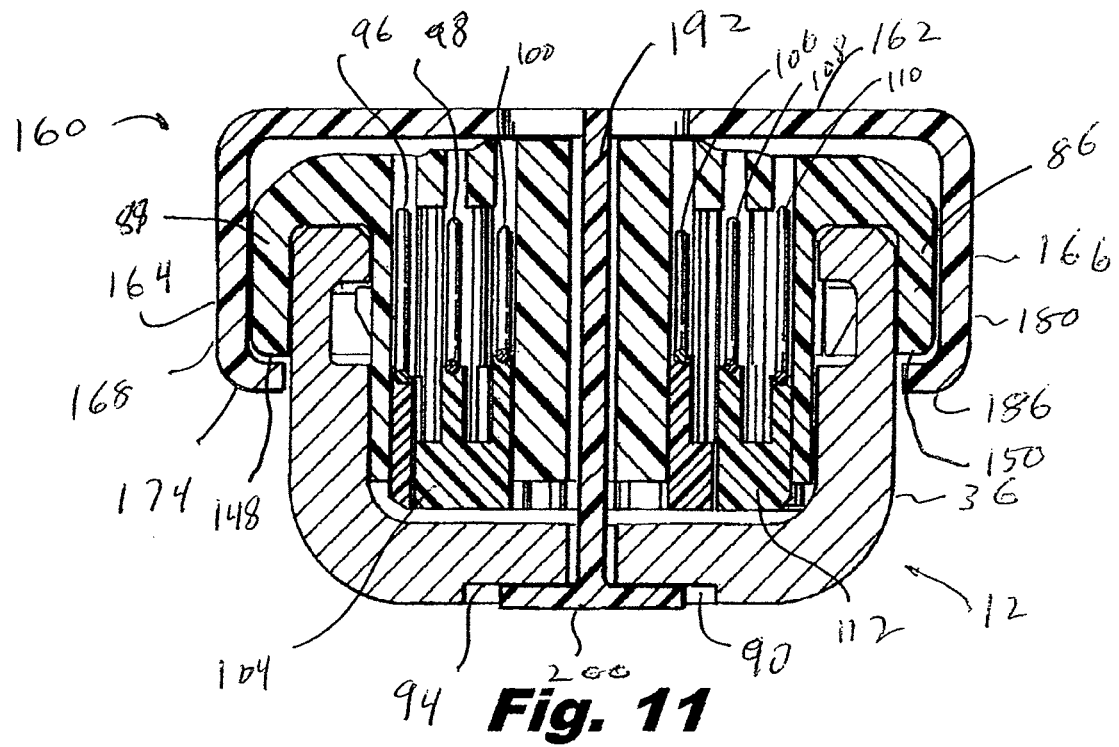
FIG. 11 is a cross sectional view of the cartridge shipping aid of FIG. 10 positioned on a staple cartridge.

Referring now to FIGS. 10 and 11, there is disclosed a still further alternative embodiment of a cartridge shipping aid 160. Although the shipping aid 160 has a curved shape in FIGS. 10 and 11, rectangular and other shapes are contemplated. Cartridge shipping aid 160 includes a base 162 having first and second sidewalls 164 and 168 projecting downwardly and perpendicularly from base 162. In this embodiment, a plurality of downward projections 168, 170 and 172 extends from first sidewall 164 and include respective inwardly directed lips 174, 176 and 178 which are configured to engage bottom edge 150 on insert 34. Likewise, second sidewall 166 includes downward projections 180, 182 and 184 also having respective inwardly directed lips 186, 188 and 190 which are configured to engage bottom edge 148 of insert 34.

With continued reference to FIGS. 10 and 11, cartridge shipping aid 160 additionally includes a plurality of ribs 192, 194 and 196 which extends from an undersurface 198 of base 162 and parallel to first and second sidewalls 164 and 166. Ribs 192, 194 and 196 terminate in respective perpendicular keys 200, 202 and 204 which are received within horizontal slot 90 of outer channel member 36 and which function substantially identical to keys 70-74 described herein above with respect to cartridge shipping aid 10 to engage bottom surface 94 of outer channel member 36 to secure cartridge shipping aid 160 against vertical movement relative to staple cartridge 12.

Thus, cartridge shipping aid 160 utilizes both a rib and key structure and an inwardly directed lips structure to firmly secure staples 96, 98 and 100 and 106, 108 and 110, along with associated pushers 104 and 112, within staple cartridge 12.

Figure 12:
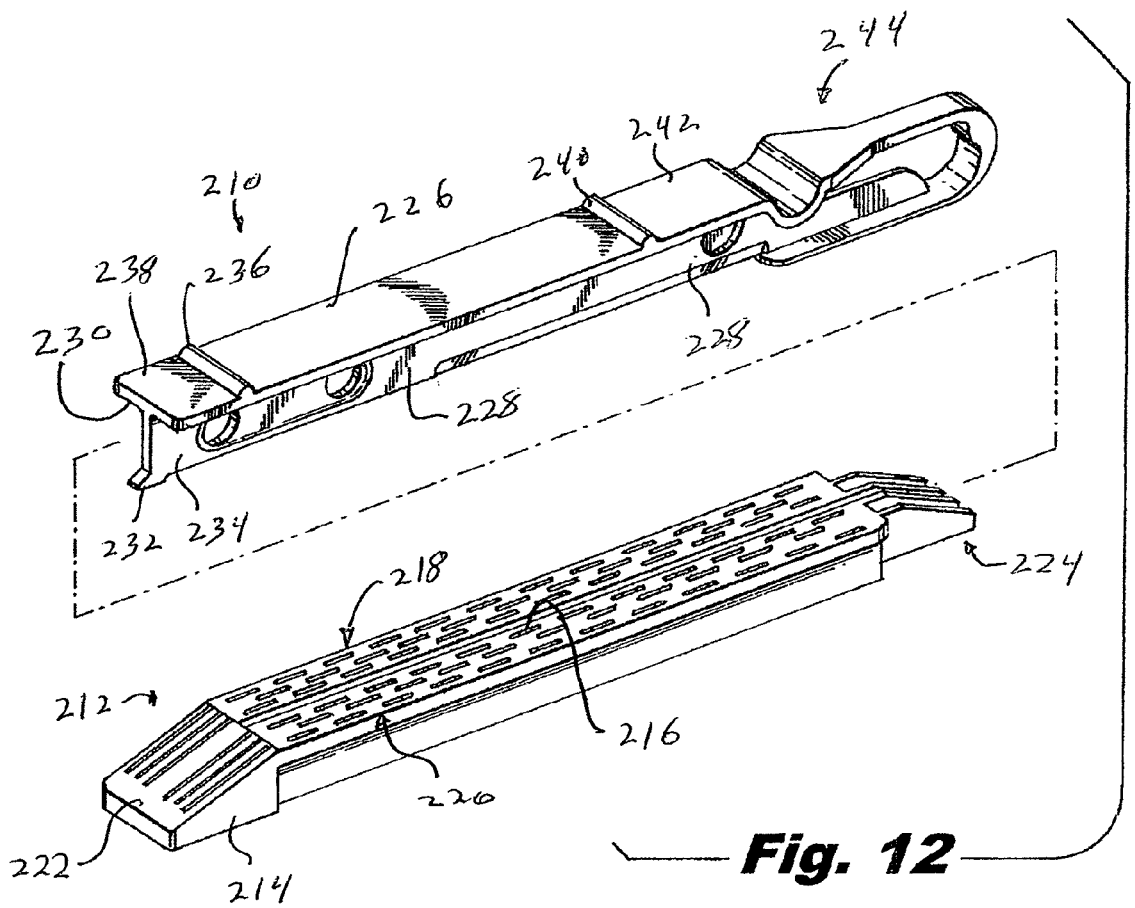
FIG. 12 is a perspective view of a still further cartridge shipping aid and an alternative staple cartridge.

Referring now to FIGS. 12-21, there is disclosed a further alternate embodiment of a cartridge shipping aid 210 for use with a straight staple cartridge 212. Referring initially to FIG. 12, staple cartridge 212 is shown without an outer channel member and includes a straight insert 214 having a longitudinally extending knife slot 216. Similar to staple cartridge 12 described herein above, straight insert 214 includes a plurality of longitudinally extending staggered rows of staple pockets 218 and 220 on either side of knife slot 216. Straight insert 214 includes an angled leading edge 222 and a trailing end 224.

Figure 13:
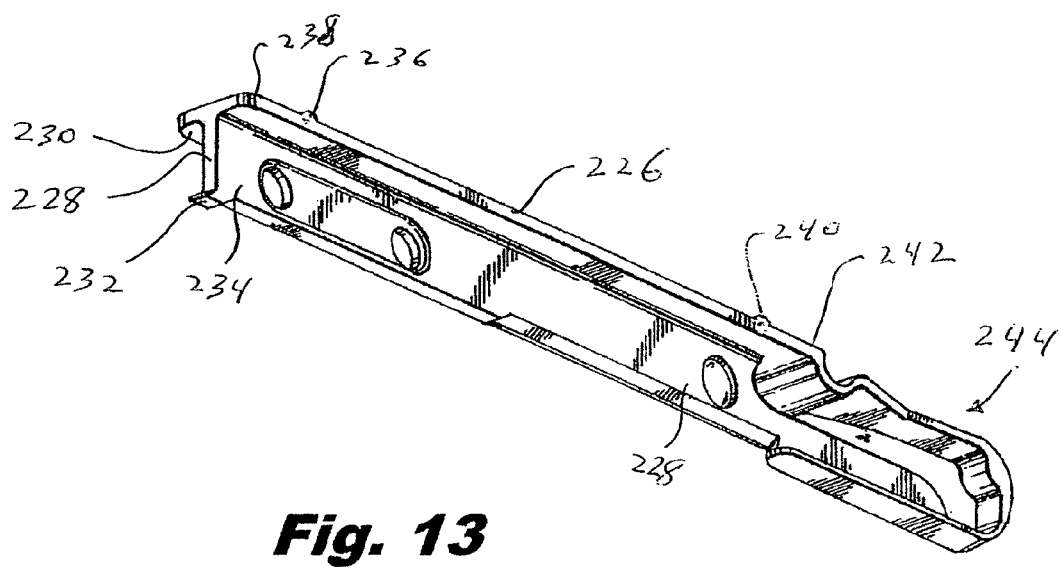
FIG. 13 is another perspective view of the cartridge shipping aid of FIG. 12.

Referring to FIGS. 12 and 13, cartridge shipping aid 210 includes a longitudinally extending base 226 having a longitudinal rib 228 extending perpendicularly from an underside 230 of base 226. A leading tooth 232 is provided at a distal end 234 of rib 228 to guide rib 228 into knife slot 216 in straight insert 214. A first finger bump 236 is provided on a distal end 238 of base 226 and a second finger bump 240 is provided on a proximal end 242 of base 226. First and second finger bumps 236 and 240 are provided to facilitate advancing cartridge shipping aid 210 through straight insert 214. Grasping and securing structure 244 is provided at a proximal end 246 of rib 228 and proximal end 242 of base 226 and is described in more detail hereinbelow.

Figure 14:
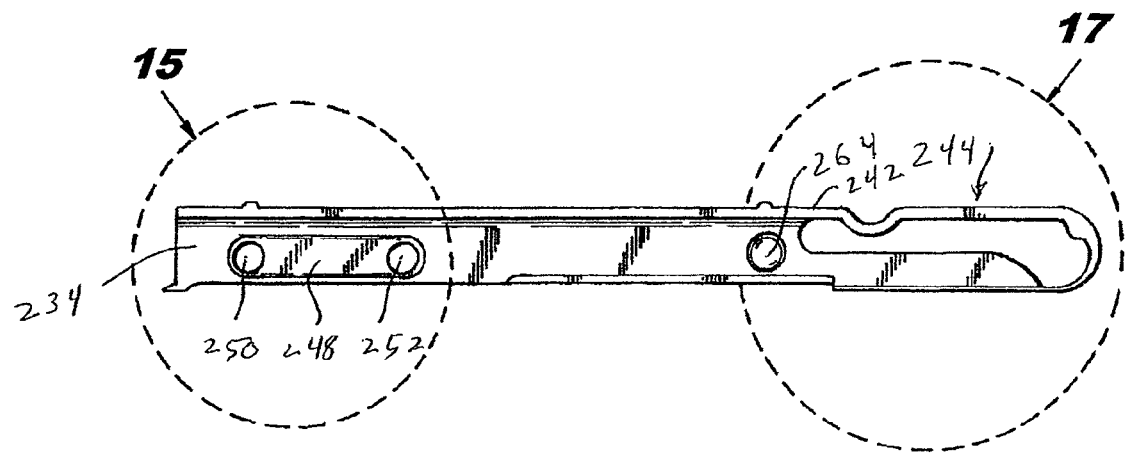
FIG. 14 is a side view of the cartridge shipping aid of FIG. 12.
Figure 15:
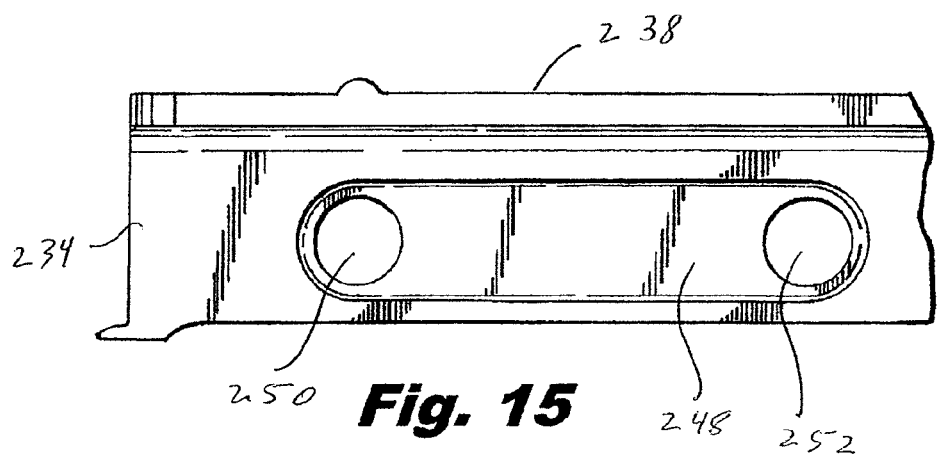
FIG. 15 is a an enlarged area of detail view of FIG. 14.

Referring now to FIGS. 14 and 15, an oval molded impression 248 is located within distal end 234 of rib 228 and includes a pair of relief holes 250 and 252 as a result of the molding or machining of cartridge shipping aid 210.

Figure 16:
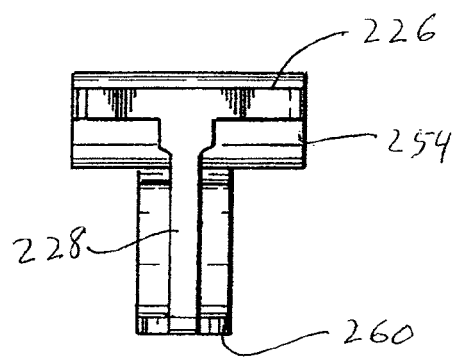
FIG. 16 is a cross sectional view of the cartridge shipping aid of FIG. 12.
Figure 17:
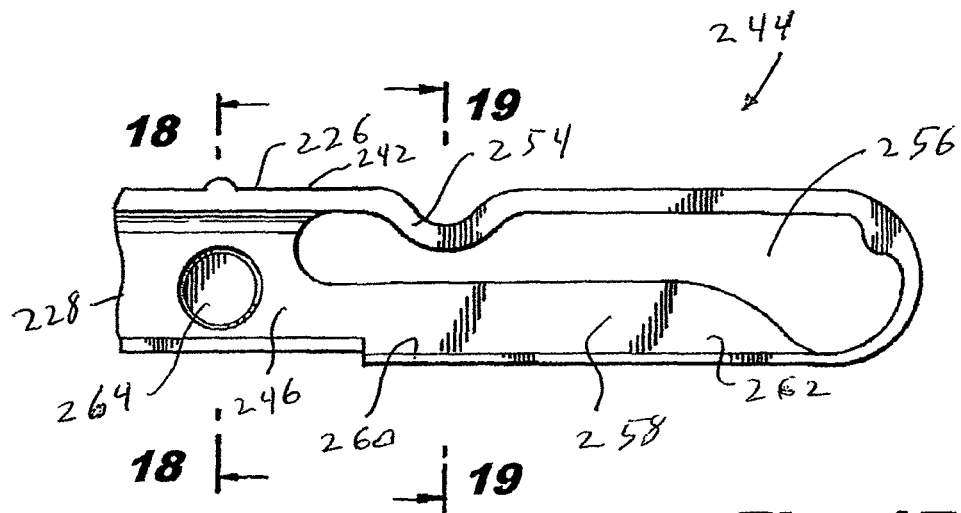
FIG. 17 is an enlarged area of detail view of FIG. 14.

Turning now to FIGS. 14, 16 and 17, grasping and securing structure 244 extends proximally from respective proximal ends 242, 246 of base 226 and rib 228. Specifically, grasping and securing structure 244 extends proximally from a proximal end 242 of base 226 at a transitional bump 254. With specific reference to FIG. 17, a cut out 256 is formed within grasping and securing structure 244 to facilitate grasping by the fingers of the user.

Figure 19:
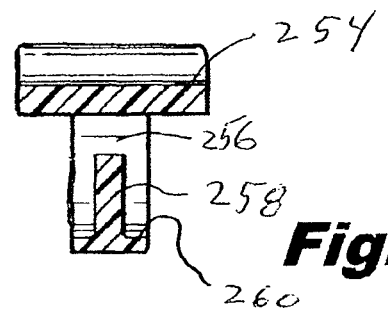
FIG. 19 is a cross sectional view taken along line 19-19 of FIG. 17.

With specific reference to FIGS. 17 and 19, a rib extension 258 extends into cut out 256 and a lower flange 260 extends along a bottom edge 266 of rib extension 258.

Figure 18:
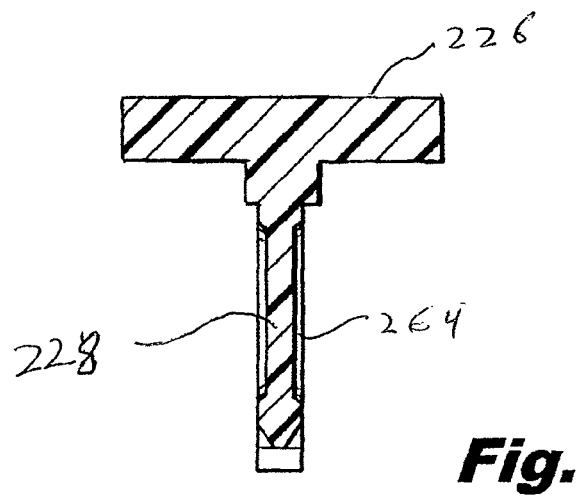
FIG. 18 is a cross sectional view taken along line 18-18 of FIG. 17.

As best shown in FIGS. 14, 17 and 18, a relief hole or depression 264 is formed within proximal end 246 of rib 228 during molding or manufacturing.

Figure 20:
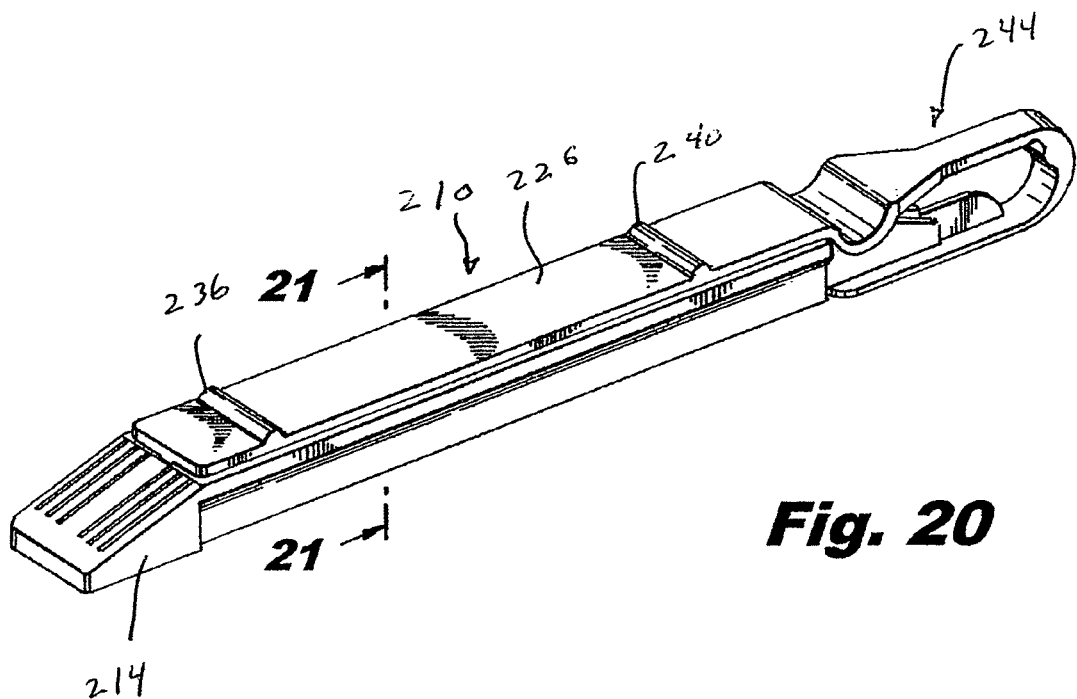
FIG. 20 is a perspective view of the cartridge shipping aid of FIG. 12 positioned on the alternative staple cartridge.

Referring now to FIG. 20, in order to assemble cartridge shipping aid 210 to staple cartridge 212, additionally, leading tooth 232 on rib 228 (FIG. 12) is inserted into knife slot 216 in straight insert 214. Thereafter, the user or person assembling the components can press their fingers against first and second finger bumps 236 and 240 to further advance rib 228 within knife slot 216. Staple cartridge aid 210 is advanced relative to straight insert until transitional bump 254, on grasping and securing structure 244, engages trailing end 244 of straight insert 214. At this point, cartridge shipping aid 210 is properly positioned on straight insert 214 of staple cartridge 212.

Figure 21:
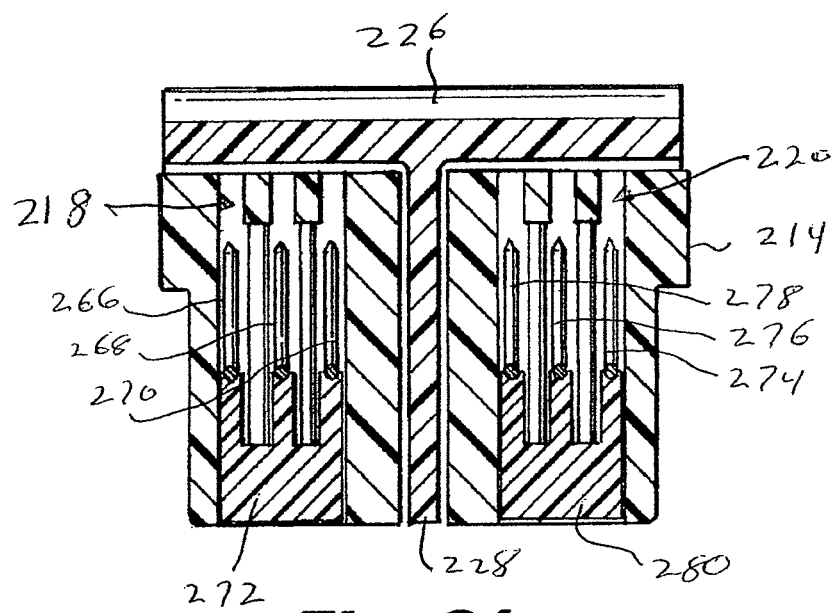
FIG. 21 is a cross sectional view taken along line 21-21 of FIG. 20.

As best shown in FIG. 21, insert 214 includes a plurality of staples 266, 268 and 270 within staple pockets 218 and which are supported within staple pockets 218 by a pusher 272. Similarly, a plurality of staples 274, 276 and 278 are provided within staple pockets 220 and are supported therein by a pusher 280. As shown, underside 230 of base 226 retains the plurality of Staples, and associated pushers, within their respective staple pockets.

While not specifically shown, an outer channel member associated with staple cartridge 212 is provided to support straight insert 214 and may include a bottom channel or plate similar to horizontal slot 90 disclosed herein above with respect to staple cartridge 12. Where a bottom channel is present, cartridge shipping aid 210 may be further advanced along staple cartridge 212 such that lower flange 260 of grasping and receiving structure 244 enters the bottom channel and prevents cartridge shipping aid 210 from being lifted vertically off staple cartridge 212 in a manner similar to that disclosed herein above with regard to perpendicular keys formed along a bottom edge of the disclosed ribs.

Referring to FIG. 20, in order to remove cartridge shipping aid 210 from straight insert 214 of staple cartridge 212, grasping and securing structure 214 is grasped by the user and cartridge shipping aid 210 maybe pulled longitudinally to draw rib 228 out of knife slot 216 or may be lifted vertically to lift longitudinal rib 228 out of knife slot 216.

The shipping aid 210, although shown in FIGS. 12 and 13 with a linear shape, may be curved to cooperate with a curved cartridge, or may have some other shape.

The present disclosure also contemplates a staple cartridge assembly including a removable shipping/handling aid, the removable shipping /handling aid being in accordance with the embodiment of FIGS. 1-7, or FIGS. 8-9, or FIGS. 10-11, or FIGS. 12-21, and the assembly having a staple cartridge with an insert and a plate or channel. The staple cartridge houses a plurality of surgical staples and may include one or more pushers for driving the staples against the anvil.

It will be understood that various modifications may be made to the embodiments disclosed herein. For example, the structure of the disclosed cartridge shipping aid including a base having a rib extending perpendicularly from a base may assume shapes other than straight or arcuate such as, for example, circular for use with circular surgical staplers, etc. Further, more or less perpendicular keys may be provided along the underside of the disclosed ribs. Therefore, the above description should not be construed as limiting, but merely as exemplifications of particular embodiments. Those skilled in the art will envision other modifications within the scope and spirit of the claims appended hereto.

The invention claimed is:

1. A staple cartridge comprising:
   a channel member;
   an insert disposed within the channel member, the insert including first and second projection halves defining a slot therebetween; and
   a shipping aid selectively engageable with the channel member and the insert, the shipping aid including,
   a base;
   a first side wall extending from a first edge of the base;
   a second side wall extending from a second edge of the base, wherein the channel member is received between the first side wall and the second side wall; and
   a rib extending perpendicularly from an underside of the base and received within the slot of the insert.

2. The staple cartridge as recited in claim 1, wherein the rib of the shipping aid extends parallel to the first and second side walls.

3. The staple cartridge as recited in claim 1, wherein the base of the shipping aid includes a tab extending from a first end of the base.

4. The staple cartridge as recited in claim 1, wherein the base of the shipping aid includes a T-shaped tab extending from a second end of the base.

5. The staple cartridge as recited in claim 4, wherein the T-shaped tab includes a downward projection for engagement with the insert.

6. The staple cartridge as recited in claim 5, wherein the downward projection includes at least one pin for engagement with a detent formed in the insert.

7. The staple cartridge as recited in claim 5, wherein the T-shaped tab includes a cross member and a flexible neck connecting the cross member to the second end of the base.

8. The staple cartridge as recited in claim 7, wherein the downward projection extends from the cross member.

9. The staple cartridge as recited in claim 1, wherein the base, the first side wall, the second side wall, and the rib of the shipping aid are curved.

10. The staple cartridge as recited in claim 9, wherein a radius of curvature of the base, the first side wall, the second side wall, and the rib of the shipping aid are identical to a radius of curvature of the channel member and the insert.

11. The staple cartridge as recited in claim 1, wherein the base, the first side wall, the second side wall, and the rib are of monolithic construction.

12. A staple cartridge comprising:
    a channel member;
    an insert disposed within the channel member; and
    a shipping aid selectively engageable with the channel member and the insert, the shipping aid including,
    a base;
    a first side wall extending perpendicularly from the base and having a first inwardly directed lip; and
    a second side wall extending perpendicularly from the base and having a second inwardly directed lip, the first and second inwardly directed lips selectively securing the channel member between the first and second side walls.

13. The staple cartridge as recited in claim 12, further comprising at least one rib extending perpendicularly from an underside of the base and extending parallel to the first and second side walls.

14. The staple cartridge as recited in claim 13, wherein the at least one rib is received with a slot defined by the insert.

15. The staple cartridge as recited in claim 13, wherein the at least one rib includes a plurality of longitudinally spaced ribs.

16. The staple cartridge as recited in claim 13, wherein the at least one rib includes a perpendicular key formed on a lower edge of the at least one rib.

17. The staple cartridge as recited in claim 12, wherein the first side wall includes at least one downward projection, the first inwardly directed lip extending from the at least one downward projection.

18. The staple cartridge as recited in claim 17, wherein the second side wall includes at least one downward projection, the second inwardly directed lip extending from the at least one downward projection.

* * * * *